(12) United States Patent
Hagiwara et al.

(10) Patent No.: US 6,425,872 B1
(45) Date of Patent: Jul. 30, 2002

(54) SYSTEM FOR MEASURING PHYSICAL PARAMETER UTILIZING VIBRATION TRANSMISSION

(75) Inventors: Hisashi Hagiwara, Yokohama; Hiroshi Fukukita, Tokyo; Kinya Hasegawa, Sagamihara; Yushi Nishimura, Yokohama, all of (JP)

(73) Assignee: Matsushita Electric Industrial Co., Ltd. (JP)

( * ) Notice: Subject to any disclaimer, the term of this patent is extended or adjusted under 35 U.S.C. 154(b) by 48 days.

(21) Appl. No.: 09/690,821

(22) Filed: Oct. 18, 2000

(30) Foreign Application Priority Data

Oct. 20, 1999 (JP) .............................. 11-298438

(51) Int. Cl.[7] .............................................. A61B 5/00
(52) U.S. Cl. ........................................ 600/485; 600/500
(58) Field of Search ................................ 600/485, 450, 600/453–6, 500

(56) References Cited

U.S. PATENT DOCUMENTS

| | | | | |
|---|---|---|---|---|
| 4,771,792 A | * | 9/1988 | Seale | 600/483 |
| 5,241,963 A | * | 9/1993 | Shankar | 600/481 |
| 5,590,649 A | | 1/1997 | Caro et al. | 128/630 |
| 5,791,347 A | * | 8/1998 | Flaherty | 600/500 |
| 5,810,734 A | * | 9/1998 | Caro et al. | 600/500 |
| 5,830,131 A | * | 11/1998 | Caro et al. | 600/500 |
| 5,833,618 A | * | 11/1998 | Caro et al. | 600/500 |

FOREIGN PATENT DOCUMENTS

JP 9-506024 6/1997

* cited by examiner

*Primary Examiner*—Robert L. Nasser
(74) *Attorney, Agent, or Firm*—Parkhurst & Wendel, L.L.P.

(57) ABSTRACT

A physical parameter measuring system is provided which measures a physical parameter such as a blood pressure of a person using oscillation transmission. The system includes a phase detector, an A/D converter, an arc center determining circuit, and a phase angle determining circuit. The phase detector detects a phase of a sensor signal produced, in sequence, by monitoring oscillations which are applied by an exciter and transmitted through a living body to map the signal on a two-dimensional plane as a sample point. The A/D converter converts the sample point signal into a digital sample point signal in sequence. The arc center determining circuit determines a center of an arc defined by a distribution of the sample points mapped for a given period of time. The arc determining circuit selects the sample points which are located at an interval greater than a given reference sample-to-sample distance to form a sample group consisting of at least three of the selected sample points and determines a center of a circle passing through the sample group as the center of the arc. The phase angle determining circuit determines a phase angle of the sample point as viewed from the arc center determined by the arc center determining circuit and provides it as a parameter used to determine a physical parameter of the subject.

20 Claims, 7 Drawing Sheets

SYSTEM FOR MEASURING PHYSICAL PARAMETER UTILIZING VIBRATION TRANSMISSION

BACKGROUND OF THE INVENTION

1. Technical Field of the Invention

The present invention relates generally to a physical parameter measuring system which applies oscillations to a blood vessel in a person or subject and samples and analyzes the oscillations transmitted through the blood vessel to obtain living body information noninvasively, and more particularly to an improvement on a physical parameter measuring system designed to obtain living body information in the form of a parameter derived based on the center of an arc defined by mapping on a two-dimensional plane samples of the transmitted oscillations moving backward and forward in time sequence.

2. Background Art

As typical noninvasive systems for measuring the blood pressure, an oscillometric system a Korotkoff system are known. The oscillometric system is designed to exert pressure on a patient's upper arm using a cuff and changing the pressure to monitor a change in amplitude of a resulting pulsation corresponding to the blood pressure. The Korotkoff system is designed to detect Korotkoff sounds produced from a blood vessel on which pressure is exerted by a cuff to determine the blood pressure. These systems, however, require approximately thirty seconds for one measurement and are useless in an emergency case where it is necessary to monitor a sudden change in blood pressure of a patient on the operating table.

U.S. Pat. No. 5,590,649 issued on Jan. 7, 1997 discloses a blood pressure determining system designed to avoid the above problem. The system detects the elasticity of a blood vessel which will change as a change in blood pressure to determine the blood pressure and will be described below in detail with reference to FIGS. 8 and 9.

Figure 8:
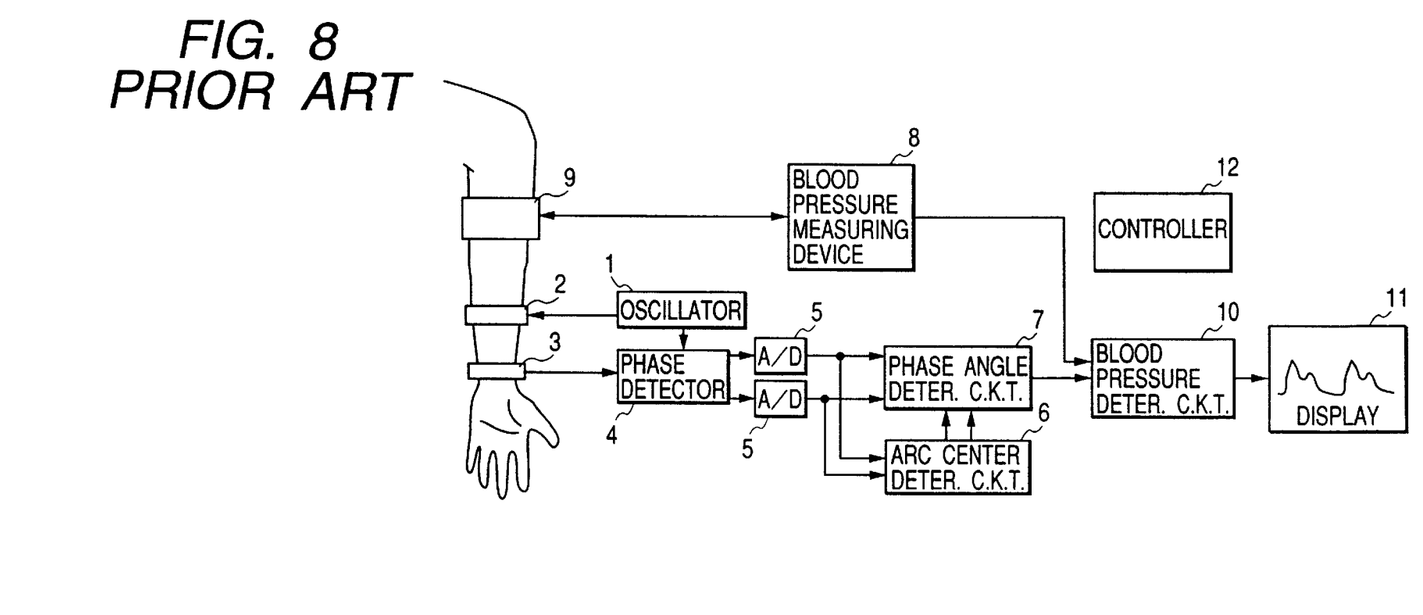
FIG. 8 is a block diagram which shows a circuit structure of a conventional blood pressure measuring system.

The system includes generally an oscillator 1, an exciter 2, a sensor 3, a phase detector 4, and A/D converters 5. The oscillator 1 generates a since wave of several tens Hz to oscillate an artery of a patient through the exciter 2 attached to a patient's arm. The sensor 3 detects oscillations transmitted through the artery and converts them into an electric signal. The phase detector 4 compares the relative phase between the output of the sensor 3 and a reference signal that is the output of the oscillator 1 to produce an in-phase component signal (also referred to as an I-signal below) and a quadrature component signal (also referred to as a Q-signal below). The I-signal and Q-signal outputted from the phase detector 4 are converted by the A/D converters 5 into digital signals and inputted to a phase angle determining circuit 7 and an arc center determining circuit 6. The arc center determining circuit 6 determines the center of distribution of inputs and outputs x- and y-coordinates thereof to the phase angle determining circuit 7. The phase angle determining circuit 7 calculates phase angles of the I-signal and the Q-signal as viewed from the center of the distribution. A blood pressure measuring 8 actuates a cuff 9 at given time intervals and outputs systolic and diastolic blood pressure values to a blood pressure determining circuit 10. The blood pressure determining circuit 10 determines a relation among the systolic and diastolic pressure values and the phase angle determined by the phase angle determining circuit 7 at the instant when the blood pressure measuring device 8 starts to operate, which will be referred to as calibration below. After such calibration, the blood pressure determining circuit 10 determines the blood pressure only based on the phase angle determined by the phase angle determining circuit 7 and outputs it in the form of a continuous wave signal to the display 11. The control circuit 12 are connected to the above described system components to control operations thereof.

Figure 9:
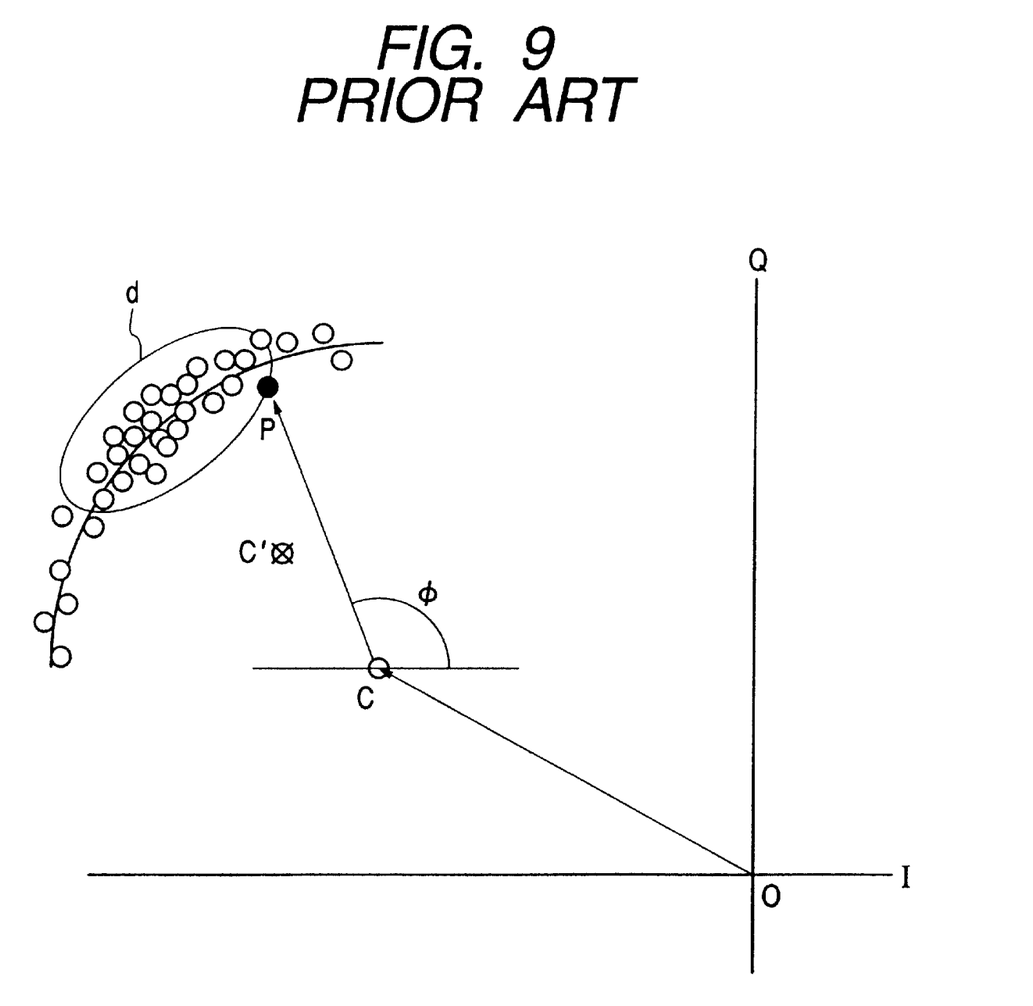
FIG. 9 is an illustration which shows how to determine a phase angle of each sample as viewed from the center of an arc defined by a set of samples in the system of FIG. 8.

If the I-signals and the Q-signals digitized by the phase detector 4 are defined as representing x-coordinates and y-coordinates on a two-dimensional plane, respectively, then they are distributed, as shown in FIG. 9, along an arc. Specifically, the signals outputted from the A/D converters 5 may be used as coordinate data indicating x- and y-coordinates of a sample data (i.e., the detected oscillation). A vector from the origin to each plotted sample point represents the phase and amplitude of a waveform of the oscillation transmitted through the arm of the patient and may be separated into two components: one is an oscillation component transmitted through the blood vessel, that is, a vector from the arc center C, as shown in FIG. 9, to each sample P and the other is an oscillation component transmitted through tissue other then the blood vessel, that is, a vector from the origin O to the arc center C.

Since the tissue other then the blood vessel are not moved, the oscillation component transmitted through the tissue is fixed or stays at the arc center C, while the oscillation component transmitted through the blood vessel has the phase which increases when the blood pressure is high because the elasticity of the blood vessel is sensitive to the blood pressure so that it increases with an increase in blood pressure, thus resulting in quick transmission of the oscillation and decreases when the blood pressure is low because the elasticity of the blood vessel decreases with a decrease in blood pressure, thus resulting in slow transmission of the oscillation. Specifically, the samples move, in time sequence, from one end of the arc to and return from the other end of the arc in each cycle of change in blood pressure or one heartbeat. The phase angle of the sample P, as viewed from the arc center C, has a one-to-one correspondence to the blood pressure. It is, thus, possible to have the systolic pressure Psys and the diastolic pressure Pdias measured by the blood pressure determining circuit 8 bear a one-to-one correspondence to the maximum value φ sys and the minimum value φ dias of the phase angle immediately before or after actuation of the cuff 9, respectively. Assuming that the pressure difference between Psys and Pdias is proportional to the phase angle difference between φ sys and φ dias, we obtain $$P = \frac{Psys - Pdias}{\phi sys - \phi dias}(\phi - \phi dias) + Pdia \tag{1}$$

where P is the blood pressure at an phase angle of φ.

It is important for precise measurement of the blood pressure in the above system to determine the arc center C of a distribution of samples with high accuracy, but U.S. Pat. No. 5,590,649 is silent about the algorithm for determining the arc center C. The arc center C may be determined by defining a circle using three samples on the arc and calculate the center of the circle mathematically. The samples derived at regular time intervals usually concentrate in an area d, as shown in FIG. 9. Thus, if the number of samples is decreased to 1/n, and the circle is defined by three selected samples adjacent in time each other, a disadvantage is encountered that a point C', as shown in FIG. 9, closer to the arc is determined as the center C due to noise components in the area d. Further, if the selected samples are too close to each other, a segment defined thereby may be a straight line, thus resulting in difficulty in determining the center of the distribution of the samples accurately.

SUMMARY OF THE INVENTION

It is therefore a principal object of the present invention to avoid the disadvantages of the prior art.

It is another object of the present invention to provide a blood pressure measuring system designed to determine the above described center of an arc needed to measure the blood pressure with high accuracy.

According to one aspect of the invention, there is provided a physical parameter measuring system comprising: (a) an exciter applying oscillations to a subject; (b) a sensor monitoring the oscillations propagated through the subject to provide a signal indicative thereof in sequence; (c) a phase detector detecting a phase of the signal outputted from the sensor to map, in sequence, the signal on a two-dimensional plane as a sample point and providing a sample point signal indicative thereof; (d) an A/D converter converting the sample point signal into a digital sample point signal in sequence; (e) an arc center determining circuit determining a center of an arc defined by a distribution of the sample points mapped for a given period of time, the arc center determining circuit including a sample group selecting circuit selecting the sample points which are located at an interval greater than a given reference sample-to-sample distance to form a sample group consisting of at least three of the selected sample points, and a circle center determining circuit determining a center of a circle passing through the sample group as the center of the arc; and (f) a phase angle determining circuit determining a phase angle of the sample point as viewed from the arc center determined by the arc center determining circuit and providing it as a parameter used to determine a physical parameter of the subject.

In the preferred mode of the invention, the arc center determining circuit also includes a reference distance determining circuit determining the reference sample-to-sample distance according to a given algorithm.

The reference distance determining circuit determines the reference sample-to-sample distance based on the center of the distribution of the sample points.

The sample group selecting circuit forms a plurality of sample groups each consisting of at least three of the selected sample points which are located at the interval away from each other. The circle determining circuit determines centers of circles passing through the sample groups and finds a middle of the centers as the center of the arc.

The subject is a living body. The physical parameter of the subject is a physiological parameter produced by heartbeat motion of the living body.

The reference distance determining circuit includes a center determining circuit determining a center of the distribution of the sample points derived for a time period more than or equal to one cycle of heartbeats, a maximum value determining circuit determining a maximum value of distances between the center of the distribution and the sample points derived for a time period more than or equal to the one cycle of heartbeats, respectively, and a monotone increasing function circuit determining as the reference sample-to-sample distance a value of a monotone increasing function taking the maximum value as a variable.

The maximum value determining circuit may determine as the maximum value the nth (n is two or more) greatest of the distances between the center of the distribution and the sample points.

The monotone increasing function is a proportional function.

A constant of proportion in the proportional function ranges from ⅓ to 2.

A low-pass filter may also be provided which filters the center of the circle passing through the sample group.

According to another aspect of the invention, there is provided a physical parameter measuring method comprising the steps of: (a) applying oscillations to a subject; (b) monitoring the oscillations propagated through the subject to provide a signal indicative thereof in sequence; (c) detecting a phase of the signal to map, in sequence, the signal on a two-dimensional plane as a sample point and providing a sample point signal indicative thereof; (d) converting the sample point signal into a digital sample point signal in sequence; (e) determining a center of an arc defined by a distribution of the sample points mapped for a given period of time, the arc determining step including selecting the sample points which are located at an interval greater than a given reference sample-to-sample distance to form a sample group consisting of at least three of the selected sample points, and determining a center of a circle passing through the sample group as the center of the arc; and (f) determining a phase angle of the sample point as viewed from the arc center determined by the arc center determining circuit and providing it as a parameter used to determine a physical parameter of the subject.

The arc center determining step also includes a reference distance determining step of determining the reference sample-to-sample distance according to a given algorithm.

The reference distance determining step determines the reference sample-to-sample distance based on the center of the distribution of the sample points.

The sample group selecting step forms a plurality of sample groups each consisting of at least three of the selected sample points which are located at the interval away from each other, and wherein the circle determining step determines centers of circles passing through the sample groups and finds a middle of the centers as the center of the arc.

The subject is a living body, and the physical parameter of the subject is a physiological parameter produced by heartbeat motion of the living body.

The reference distance determining step includes a center determining step of determining a center of the distribution of the sample points derived for a time period more than or equal to one cycle of heartbeats, a maximum value determining step of determining a maximum value of distances between the center of the distribution and the sample points derived for a time period more than or equal to the one cycle of heartbeats, respectively, and a monotone increasing function step of determining as the reference sample-to-sample distance a value of a monotone increasing function taking the maximum value as a variable.

The maximum value determining step determines as the maximum value the nth (n is two or more) greatest of the distances between the center of the distribution and the sample points.

The monotone increasing function is a proportional function.

A constant of proportion in the proportional function ranges from ⅓ to 2.

A low-pass filtering step is further provided which filters the center of the circle passing through the sample group.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
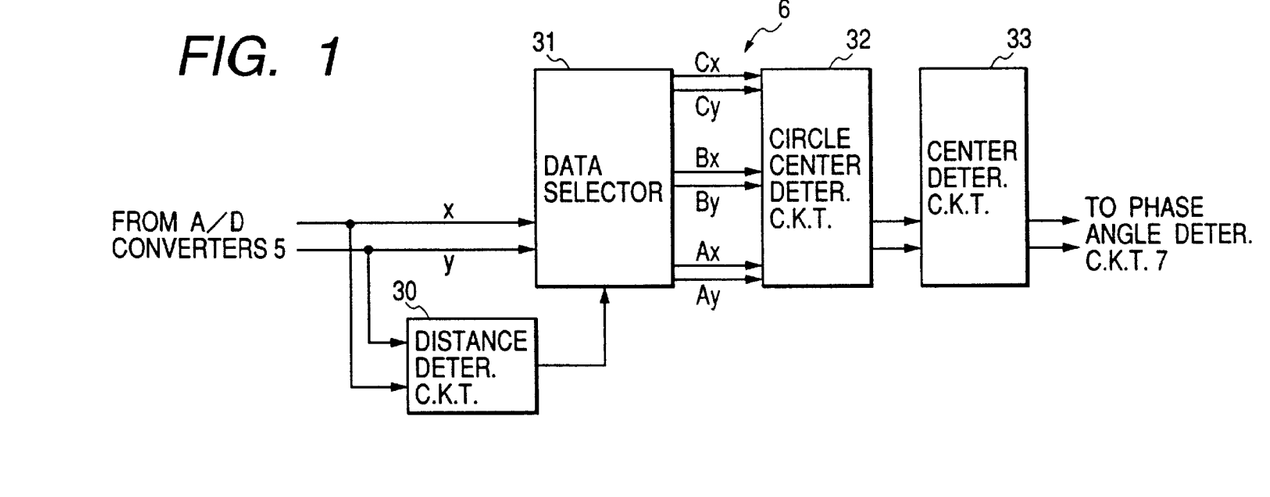
FIG. 1 is a block diagram which shows a circuit structure of an arc center determining circuit of a blood pressure measuring system according to the first embodiment of the invention.

Referring now to the drawings, wherein like numbers refer to like parts in several views, particularly to FIG. 1, there is shown a blood pressure measuring system according to the first embodiment of the invention which is designed to select some of samples which are separate in time sequence from each other with a given interval for use in determining the center of an arc defined by the samples on a two-dimensional plane.

The system of this embodiment is different in structure from the one shown in FIG. 8 (i.e., the system taught in U.S. Pat. No. 5,590,649 disclosure of which is incorporated herein by reference) only in function of the arc center determining circuit 6. Other arrangements are identical, and explanation thereof in detail will be omitted here.

The arc center determining circuit 6 includes a sample-to-sample distance determining circuit 30, a data selecting circuit 31, a circle center determining circuit 32, and a center determining circuit 33.

The sample-to-sample distance determining circuit 30 receives living body information samples (i.e., the I-signal and Q-signal as discussed in the introductory part of this application with reference to FIGS. 8 and 9) outputted from the A/D converters 5 to determine a minimum allowable interval between the samples to be used in calculating the center of an arc defined on the two-dimensional plane by the samples. The data selecting circuit 31 selects some of the samples which are separate from each other at the minimum allowable interval to form a sample group in a cycle. The circle center determining circuit 32 calculates the center of a circle defined by each sample group. The center determining circuit 33 determines the center of distribution of the centers of the circles derived by the circle center determining circuit 32 and provides it as an arc center to the phase angle determining circuit 7.

Figure 2:
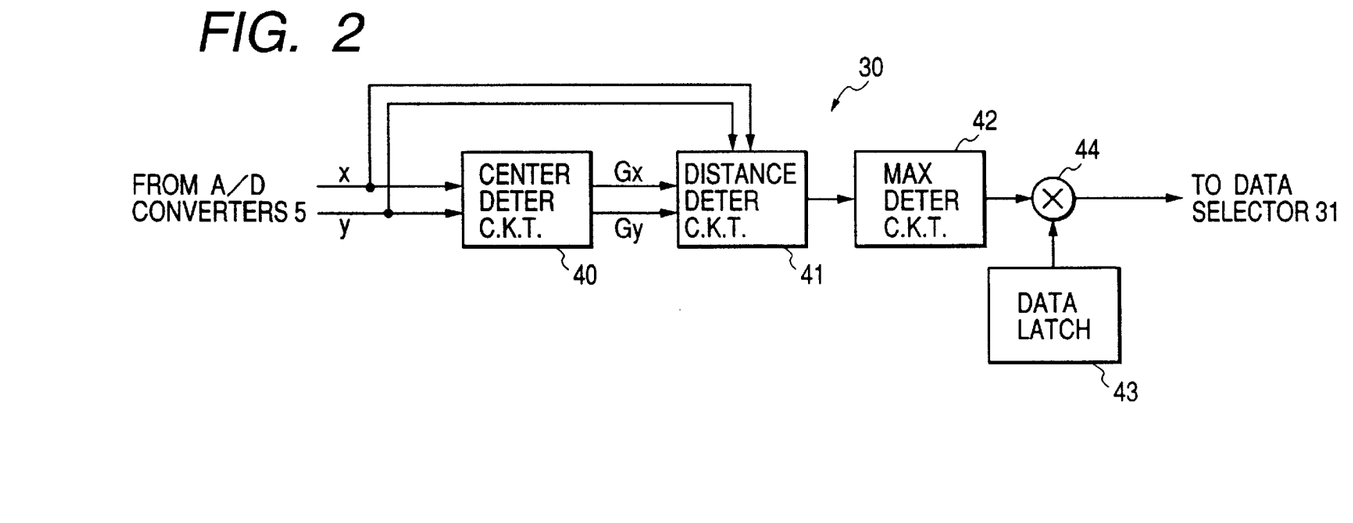
FIG. 2 is a block diagram which shows a circuit structure of a distance determining circuit of the arc center determining circuit in FIG. 1.

The sample-to-sample distance determining circuit 30 includes, as shown in FIG. 2, a center determining circuit 40, a center-to-sample distance determining circuit 41, a maximum value determining circuit 42, a data latch 43, and a multiplier 44. The center determining circuit 40 receives sample data from the A/D converters 5 to determine x- and y-coordinates (Gx, Gy) of the center of distribution of the sample data. The center-to-sample distance determining circuit 41 determines a distance between the central point defined by the coordinates (Gx, Gy) determined by the center determining circuit 40 and each of the sample data defined by coordinates (x, y) determined by the A/D converters 5. The maximum value determining circuit 42 determines a maximum value of the center-to-sample distances derived by the center-to-sample distance determining circuit 41. The data latch 43 stores therein a constant. The multiplier 44 determines the product of the maximum distance derived by the maximum value determining circuit 42 and the constant stored in the data latch circuit 43 as the minimum allowable interval and provides a signal indicative thereof to the data selecting circuit 31.

Figure 3:
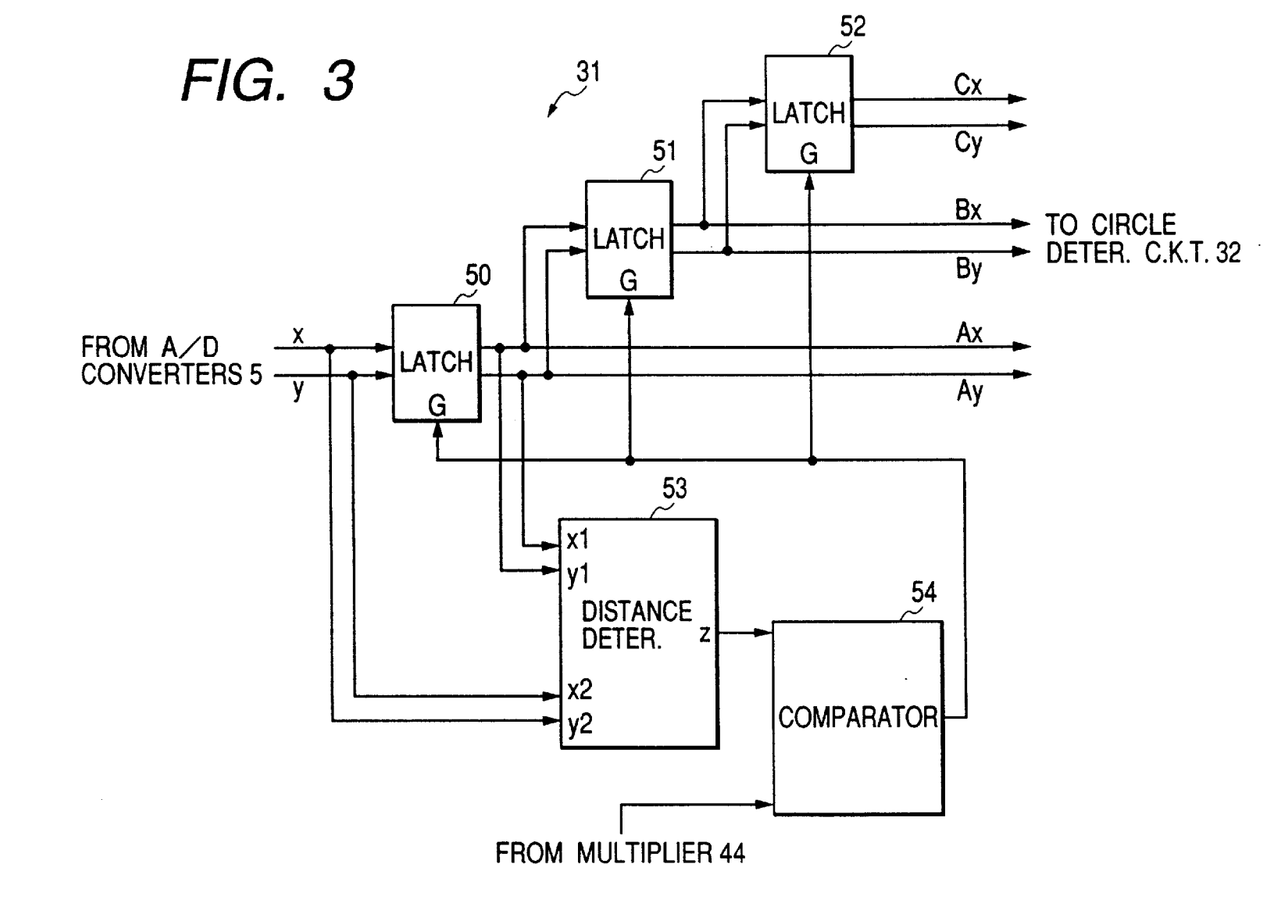
FIG. 3 is a block diagram which shows a data selecting circuit of the arc center determining circuit in FIG. 1.

The data selecting circuit 31 includes, as shown in FIG. 3, latches 50, 51, and 52, a sample-to-sample distance determining circuit 53, and a comparator 54. The latches 50, 51, and 52 store therein coordinate data.

The operation of the blood pressure measuring system of the first embodiment will be described below.

First, the center determining circuit 40 of the sample-to-sample distance determining circuit 30 determines the center of a set of sample data inputted in the past time T1. Specifically, the center determining circuit 40 calculates average values of x-coordinates and y-coordinates of the set of sample data and determines them as the x- and y-coordinates (Gx, Gy) of the center of the set of sample data. The time period T1 is a time (e.g., 2 sec.) required for one cycle of heartbeats of a person.

The center-to-sample distance determining circuit 41 determines the distance between the center (Gx, Gy) of the set of sample data and each of the sample data (x, y) according to Eq. (2) below.

$$S=\sqrt{(x-Gx)^2+(y-Gy)^2} \qquad (2)$$

The maximum value determining circuit 42 determines a maximum value Smax of a set of the distances S calculated by the center-to-sample distance determining circuit 41 in the past time T2. The time T2 is more than or equal to the time (i.e., the time T1) required for one cycle of heartbeats of a person and, for example, two (2) sec. The maximum value determining circuit 42 may select nth (n is two or more) greatest of the distances S as the maximum value Smax for eliminating the influence of noise. This is because if greater some of the distances S is separate considerably from the others, it may be considered to be caused by the adverse effects of noises. The maximum value determining circuit 42 may alternatively compare the distances S with a reference value using a comparator and excludes one or some of the distances S which are greater than the reference value as being considered to include noise components.

The data latch 43 holds therein a constant k inputted from a controller (not shown). The constant k preferably ranges from 1/30 to 2. The multiplier 44 multiplies the maximum value Smax derived by the maximum value determining circuit 42 by the constant k and outputs the result to the data selecting circuit 31. Specifically, the multiplier 44 determines a reference sample-to-sample distance using a monotone increasing function taking the maximum value as a variable.

The data selecting circuit 31 includes, as described above, the latches 50, 51, and 52. Each of the latches 50 to 52 stores input data and outputs data held up to now when an enable terminal G thereof is activated. Each enable terminal G is connected to an output of the comparator 54. Specifically, each of the latches 50 to 52 stores the input data when the output of the comparator 54 is changed to an active level.

First, the latch 50 latches the coordinates (x, y) of the sample data first outputted from the A/D converters 5 as initial coordinate data. The sample-to-sample distance determining circuit 53 determines a distance z between a sample point defined by the x- and y-coordinates (x1, y2) latched in the latch 50 and a sample point defined by x- and y-coordinates (x2, y2) inputted now from the A/D converters 5 according to Eq. (3) below.

$$Z = \sqrt{(x1-x2)^2 + (y1-y2)^2} \quad (3)$$

The comparator 54 compares the output of the multiplier 44 (i.e., the reference sample-to-sample distance) with the output of the sample-to-sample distance determining circuit 53 and outputs an active level signal when the output of the sample-to-sample distance determining circuit 53 is greater than that of the multiplier 44. This causes data stored in the latches 50, 51, and 52 to be updated, so that outputs to the circle determining circuit 32 are updated. Specifically, sample coordinate pairs (Ax, Ay), (Bx, By), and (Cx, Cy) adjacent two of which are located at an interval longer than a given value (i.e., the output of the multiplier 44) are outputted from the latches 50, 51, and 52 to the circle center determining circuit 32, respectively.

The circle center determining circuit 32 determines x- and y-coordinates (Ox, Oy) of the center of a circle passing through three points defined by the outputs of the data selecting circuit 31 each time they are updated. Specifically, the central coordinates (Ox, Oy) of the circle is calculated according to Eq. (4) below.

$$\begin{bmatrix} Ox \\ Oy \end{bmatrix} = M^{-1} \begin{bmatrix} -\gamma 1 \\ -\gamma 2 \end{bmatrix} \quad (4)$$

where $$M = \begin{bmatrix} \alpha 1 & \beta 1 \\ \alpha 2 & \beta 2 \end{bmatrix}$$

Figure 4:
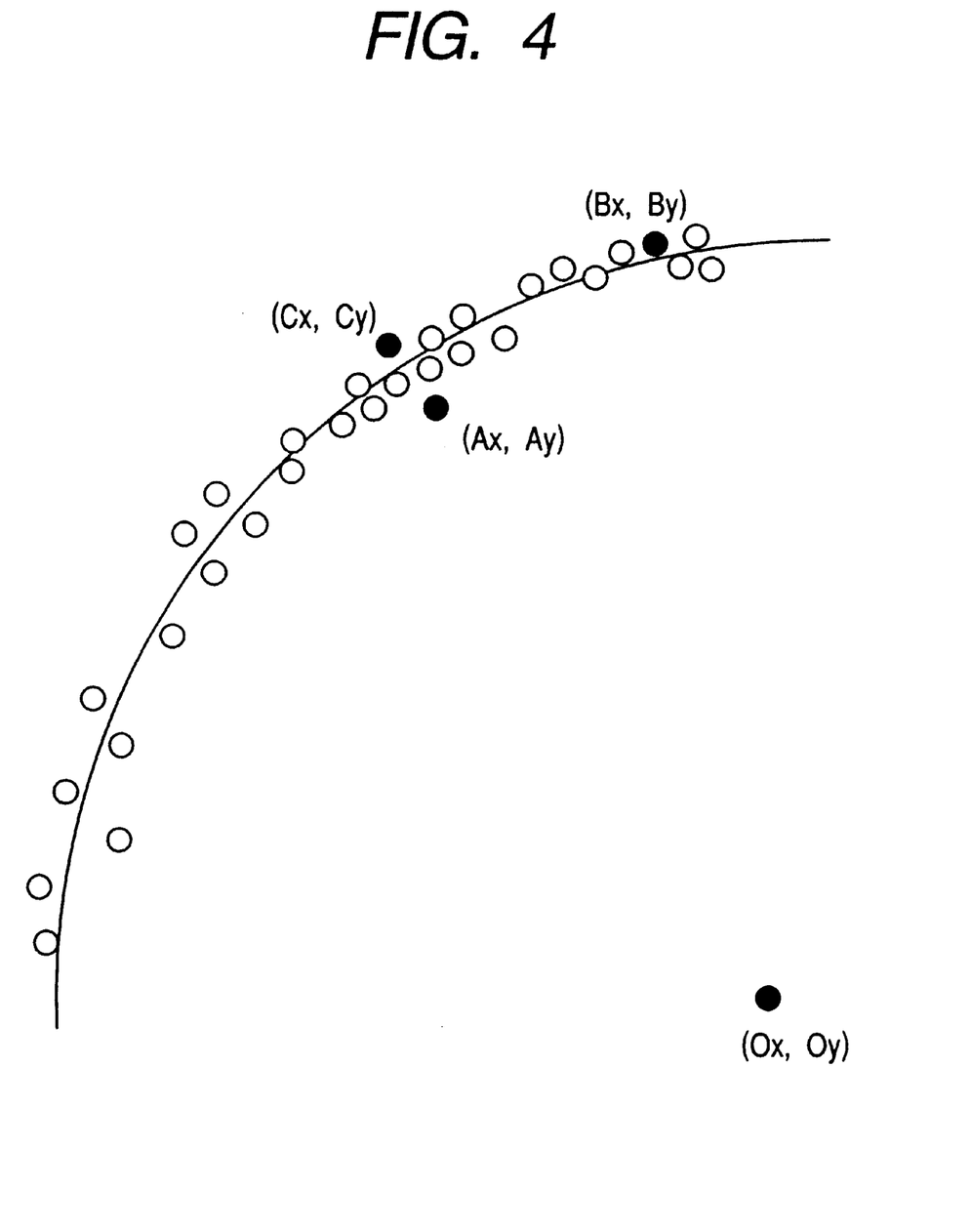
FIG. 4 is an illustration which shows an arc defined by a distribution of samples plotted on a two-dimensional plane.

$\alpha 1 = -2Ax + 2Bx$
$\alpha 2 = -2Bx + 2Cx$
$\beta 1 = -Ay + 2By$
$\beta 2 = -2By + 2Cy$
$\gamma 1 = Ax^2 - Bx^2 + Ay^2 - By^2$
$\gamma 2 = Bx^2 - Cx^2 + By^2 - Cy^2$ The three points (Ax, Ay), (Bx, By), and (Cx, Cy) selected by the data selecting circuit 31 may be, as shown in FIG. 4, located across one end (i.e., a turning point) of an arc in time sequence. Such a case results in decrease in accuracy of determining the central coordinates (Ox, Oy) of the circle. In order to avoid this problem, the circle center determining circuit 32 calculates the inner product of vectors AB and BC according to Eq. (5) below $$\vec{AB} \cdot \vec{BC} = (Bx - Ax)(Cx - Bx) + (By - Ay)(Cy - By) \quad (5)$$

The circle center determining circuit 32 finds the center of the circle only when the inner product derived by Eq. (5) is positive and ignores input data when the inner product is negative.

The center determining circuit 33 latches an input each time the output of the circle center determining circuit 32 is updated and determines the center of distribution of the central points of the circles defined by the coordinates (Ox, Oy) inputted from the circle center determining circuit 32 in the past time T3. The time T3 is more than or equal to the time required for one cycle of heartbeats of a person and, for example, two (2) sec. If the number of the central points is defined as n, and their coordinates are defined as (Ox1, Oy1), (Ox2, Oy2), (Ox3, Oy3), ..., (Oxn, Oyn), then the center (Wx, Wy) of the distribution of the central points is given as $$Wx = \frac{1}{n} \sum_{i=1}^{n} Oxi$$

$$Wy = \frac{1}{n} \sum_{i=1}^{n} Oyi$$

The center determining circuit 33 outputs the thus determined center (Wx, Wy) to the phase angle determining circuit 7, as shown in FIG. 8. Subsequent operations are the same as those discussed with reference to FIG. 7, and explanation thereof in detail will be omitted here.

Figure 5:
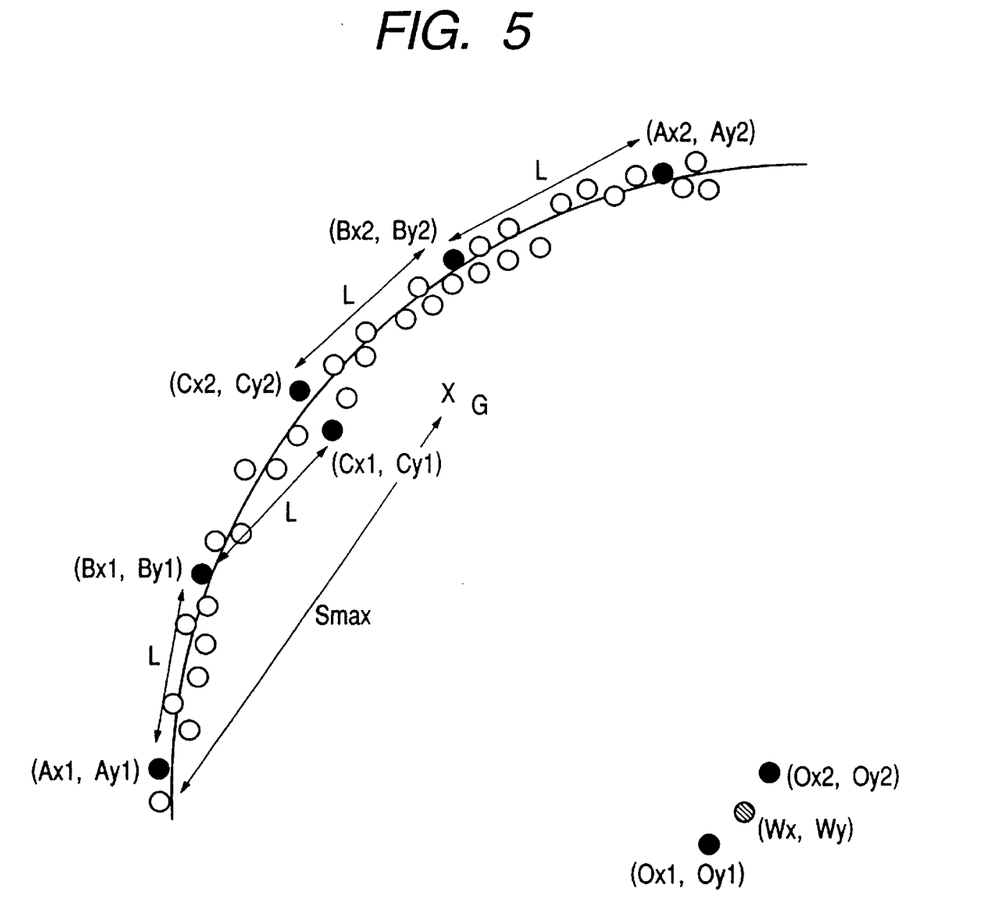
FIG. 5 is an explanatory view for explaining steps for determining an arc center.

The above operations will be explained below using a two-dimensional plane. FIG. 5 illustrates sample data outputted from the A/D converters 5 plotted on the two-dimensional plane. The point G is the center of a set of sample data determined by the center determining circuit 40. Smax indicates a maximum value of distances between the data center G and each sample data determined by the maximum value determining circuit 42. L indicates a reference distance that is an output of the multiplier 44 derived by multiplying the maximum value Smax by the constant k stored in the data latch 43. A set of sample data (Ax1, Ay1), (Bx1, By1), and (Cx1, Cy1) and a set of sample data (Ax2, Ay2), (Bx2, By2), and (Cx2, Cy2) are data groups outputted in sequence from the data selecting circuit 31. In the shown case, the distance between two of the sample data adjacent to each other in time sequence is equal to the reference distance L. The circle center determining circuit 32 determines the center (Ox1, Oy1) of a circle passing through the set of data sample (Ax1, Ay1), (Bx1, By1), and (Cx1, Cy1) and the center (Ox2, Oy2) of a circle passing through the set of data sample (Ax2, Ay2), (Bx2, By2), and (Cx2, Cy2), respectively. The center determining circuit 33 determines the center (Wx, Wy), as described above, using the centers (Ox1, Oy1) and (Ox2, Oy2).

The center-to-sample distance determining circuit 41 and the sample-to-sample distance determining circuit 53 may use the sum of a square of a difference between x-coordinates and a square of a difference between y-coordinates of data in determining the distance without calculating the square root of the sum. This results in a decrease in operation load.

As apparent from the above discussion, the blood pressure measuring system of this embodiment is designed to select sample data adjacent two of which are located at an interval greater than a given reference distance, thereby allowing the arc center to be determined accurately regardless of a change in amplitude of input data.

Figure 6:
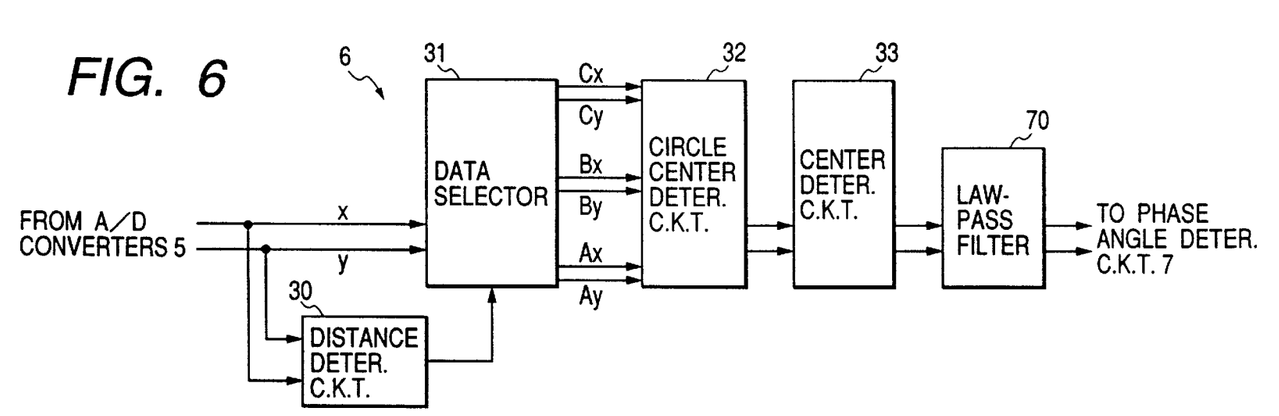
FIG. 6 is a block diagram which shows a circuit structure of an arc center determining circuit of a blood pressure measuring system according to the second embodiment of the invention.

FIG. 6 shows a blood pressure measuring system according to the second embodiment of the invention which is different from the first embodiment only in a low-pass filter 70. Other arrangements are identical, and explanation thereof in detail will be omitted here.

The low-pass filter 70 works to remove noise components from outputs of the center determining circuit 33 indicating x- and y-coordinates of the center of a circle. The cutoff frequency of the low-pass filter preferably ranges from several Hz to several tens Hz because an averaged value of the centers of a plurality of circles determined by the center determining circuit 33 should not be changed essentially over several tens Hz, and if the averaged value is changed over several tens Hz, it must contain noise components.

Figure 7:
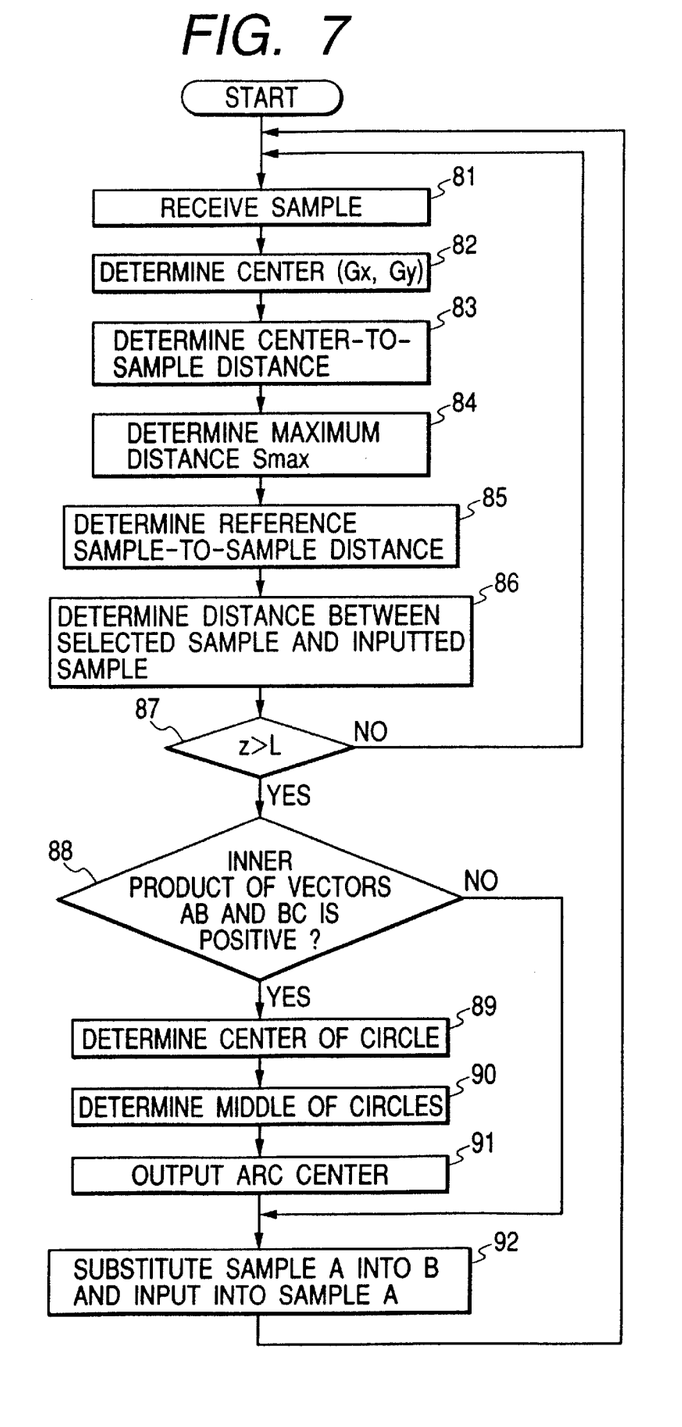
FIG. 7 is a flowchart of a program performed by an arc center determining circuit according to the third embodiment of the invention.

FIG. 7 shows a program or a sequence of logical steps performed by the arc center determining circuit 6 of a blood pressure measuring system according to the third embodiment of the invention. The arc center determining circuit 6 is implemented by a microprocessor. Other arrangements are identical with those in the first embodiment, and explanation thereof in detail will be omitted here.

After entering the program, the routine proceeds to step 81 wherein the arc center determining circuit 6 receives sample data from the A/D converters 5. The routine proceeds to step 82 wherein the center of a set of the sample data inputted in the past time T1 is calculated. Specifically, average values of x-coordinates and y-coordinates of the set of sample data are determined as the x- and y-coordinates (Gx, Gy) of the center of the set of sample data. The time period T1 is a time (e.g., 2 sec.) required for one cycle of heartbeats of a person.

The routine proceeds to step 83 wherein the distance S between the center (Gx, Gy) of the set of sample data and each of the sample data (x, y) according to the above Eq. (2).

The routine proceeds to step 84 wherein a maximum value Smax of a set of the distances S calculated in the past time T2. The time T2 is more than or equal to the time (i.e., the time T1) required for one cycle of heartbeats of a person and, for example, two (2) sec.

The routine proceeds to step 85 wherein the maximum value Smax is multiplied by a constant k to produce a reference distance L.

The routine proceeds to step 86 wherein a distance z between a point defined by the x- and y-coordinates of a sample data selected previously and a point defined by x- and y-coordinates of a sample data now inputted.

The routine proceeds to step 87 wherein it is determined whether the distance z is greater than the reference distance L or not. If a NO answer is obtained, then the routine returns back to step 81. Alternatively, if a YES answer is obtained, then the routine proceeds to step 88 wherein the inner product of a vector AB from a selected sample data A to a selected sample data B and a vector BC from the selected sample data A and the sample data (x, y) now inputted is calculated, and it is determined whether the inner product is positive or not. If it is negative, then the routine proceeds directly to step 92. Alternatively, if it is positive, then the routine proceeds to step 89.

In step 89, the selected data A and B and the inputted data (x, y) are collected into a data group in a cycle to determine the center of a circle passing through the data group.

The routine proceeds to step 90 wherein the center of distribution of the centers of the circles derived in the past time T3 is determined as an arc center. The time T3 is more than or equal to the time required for one cycle of heartbeats of a person and, for example, two (2) sec.

The routine proceeds to step 91 wherein x- and y-coordinates of the center determined in step 90 is outputted to the phase angle determining circuit 7.

The routine proceeds to step 92 wherein the selected sample data A is substituted into the selected sample data B, and the input data (x, y) is substituted into the selected sample data A and returns back to step 81. Note that a first inputted sample data is set to initial values of the selected sample data A and B.

In the third embodiment, the phase angle determining circuit 7 and the blood pressure determining circuit 10 may be implemented by the same microprocessor as the arc center determining circuit 6.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims.

What is claimed is:

1. A physical parameter measuring system comprising:

an exciter applying oscillations to a subject;

a sensor monitoring the oscillations propagated through the subject to provide a signal indicative thereof in sequence;

a phase detector detecting a phase of the signal outputted from said sensor to map, in sequence, the signal on a two-dimensional plane as a sample point and providing a sample point signal indicative thereof;

an A/D converter converting the sample point signal into a digital sample point signal in sequence;

an arc center determining circuit determining a center of an arc defined by a distribution of the sample points mapped for a given period of time, the arc center determining circuit including a sample group selecting circuit selecting the sample points which are located at an interval greater than a given reference sample-to-sample distance to form a sample group consisting of at least three of the selected sample points, and a circle center determining circuit determining a center of a circle passing through the sample group as the center of the arc; and a phase angle determining circuit determining a phase angle of the sample point as viewed from the arc center determined by said arc center determining circuit and providing it as a parameter used to determine a physical parameter of the subject.

2. A physical parameter measuring system as set forth in claim 1, wherein said arc center determining circuit also includes a reference distance determining circuit determining the reference sample-to-sample distance according to a given algorithm.

3. A physical parameter measuring system as set forth in claim 2, wherein said reference distance determining circuit determines the reference sample-to-sample distance based on the center of the distribution of the sample points.

4. A physical parameter measuring system as set forth in claim 1, wherein said sample group selecting circuit forms a plurality of sample groups each consisting of at least three of the selected sample points which are located at said interval away from each other, and wherein said circle determining circuit determines centers of circles passing through the sample groups and finds a middle of the centers as the center of the arc.

5. A physical parameter measuring system as set forth in claim 2 wherein the subject is a living body, and the physical parameter of the subject is a physiological parameter produced by heartbeat motion of the living body.

6. A physical parameter measuring system as set forth in claim 5, wherein said reference distance determining circuit includes a center determining circuit determining a center of the distribution of the sample points derived for a time period more than or equal to one cycle of heartbeats, a maximum value determining circuit determining a maximum value of distances between the center of the distribution and the sample points derived for a time period more than or equal to the one cycle of heartbeats, respectively, and a monotone increasing function circuit determining as the reference sample-to-sample distance a value of a monotone increasing function taking the maximum value as a variable.

7. A physical parameter measuring system as set forth in claim 6, wherein said maximum value determining circuit determines as the maximum value the nth (n is two or more) greatest of the distances between the center of the distribution and the sample points.

8. A physical parameter measuring system as set forth in claim 6, wherein the monotone increasing function is a proportional function.

9. A physical parameter measuring system as set forth in claim 8, wherein a constant of proportion in the proportional function ranges from ⅓ to 2.

10. A physical parameter measuring system as set forth in claim 1, further comprising a low-pass filter filtering the center of the circle passing through the sample group.

11. A physical parameter measuring method comprising the steps of:

applying oscillations to a subject;

monitoring the oscillations propagated through the subject to provide a signal indicative thereof in sequence;

detecting a phase of the signal to map, in sequence, the signal on a two-dimensional plane as a sample point and providing a sample point signal indicative thereof;

converting the sample point signal into a digital sample point signal in sequence;

determining a center of an arc defined by a distribution of the sample points mapped for a given period of time, said arc determining step including selecting the sample points which are located at an interval greater than a given reference sample-to-sample distance to form a sample group consisting of at least three of the selected sample points, and determining a center of a circle passing through the sample group as the center of the arc; and determining a phase angle of the sample point as viewed from the arc center determined by the arc center determining circuit and providing it as a parameter used to determine a physical parameter of the subject.

12. A physical parameter measuring method as set forth in claim 11, wherein said arc center determining step also includes a reference distance determining step of determining the reference sample-to-sample distance according to a given algorithm.

13. A physical parameter measuring method as set forth in claim 12, wherein said reference distance determining step determines the reference sample-to-sample distance based on the center of the distribution of the sample points.

14. A physical parameter measuring method as set forth in claim 11, wherein said sample group selecting step forms a plurality of sample groups each consisting of at least three of the selected sample points which are located at said interval away from each other, and wherein said circle determining step determines centers of circles passing through the sample groups and finds a middle of the centers as the center of the arc.

15. A physical parameter measuring method as set forth in claim 12 wherein the subject is a living body, and the physical parameter of the subject is a physiological parameter produced by heartbeat motion of the living body.

16. A physical parameter measuring method as set forth in claim 15, wherein said reference distance determining step includes a center determining step of determining a center of the distribution of the sample points derived for a time period more than or equal to one cycle of heartbeats, a maximum value determining step of determining a maximum value of distances between the center of the distribution and the sample points derived for a time period more than or equal to the one cycle of heartbeats, respectively, and a monotone increasing function step of determining as the reference sample-to-sample distance a value of a monotone increasing function taking the maximum value as a variable.

17. A physical parameter measuring method as set forth in claim 16, wherein said maximum value determining step determines as the maximum value the nth (n is two or more) greatest of the distances between the center of the distribution and the sample points.

18. A physical parameter measuring method as set forth in claim 16, wherein the monotone increasing function is a proportional function.

19. A physical parameter measuring method as set forth in claim 18, wherein a constant of proportion in the proportional function ranges from ⅓ to 2.

20. A physical parameter measuring method as set forth in claim 11, further comprising a low-pass filtering step of filtering the center of the circle passing through the sample group.

* * * * *